(12) United States Patent
Contag et al.

(10) Patent No.: US 8,349,602 B1
(45) Date of Patent: Jan. 8, 2013

(54) BIODETECTORS TARGETED TO SPECIFIC LIGANDS

(75) Inventors: Pamela R. Contag, San Jose, CA (US); David A. Benaron, Portola Valley, CA (US); Christopher H. Contag, San Jose, CA (US)

(73) Assignee: Xenogen Corporation, Alameda, CA (US)

( * ) Notice: Subject to any disclaimer, the term of this patent is extended or adjusted under 35 U.S.C. 154(b) by 426 days.

(21) Appl. No.: 08/844,336

(22) Filed: Apr. 18, 1997

Related U.S. Application Data

(60) Provisional application No. 60/015,633, filed on Apr. 19, 1996.

(51) Int. Cl.
*C12N 1/21* (2006.01)
(52) U.S. Cl. ....... 435/252.3; 435/8; 435/69.1; 435/69.6; 435/69.7
(58) Field of Classification Search ................. 536/23.1, 536/24.1, 23.7, 23.4, 23.2; 435/252.3, 8, 435/69.1, 69.6, 69.7
See application file for complete search history.

(56) References Cited

U.S. PATENT DOCUMENTS

| | | | |
|---|---|---|---|
| 4,762,701 A | 8/1988 | Horan et al. | 424/11 |
| 4,912,031 A | 3/1990 | Compton et al. | 435/7 |
| 5,281,539 A | 1/1994 | Schramm | |
| 5,283,179 A | 2/1994 | Wood | |
| 5,348,867 A | 9/1994 | Georgiou et al. | 435/69.7 |
| 5,418,132 A | 5/1995 | Olivo | 435/5 |
| 5,466,575 A | 11/1995 | Cozzette et al. | |
| 5,521,066 A * | 5/1996 | Menzel et al. | 435/7.2 |
| 5,591,604 A | 1/1997 | Fuchs et al. | 435/69.7 |
| 5,612,184 A | 3/1997 | Rosson | 435/6 |
| 5,622,868 A | 4/1997 | Clarke et al. | |
| 5,650,135 A | 7/1997 | Contag et al. | 424/9.1 |

FOREIGN PATENT DOCUMENTS

| | | |
|---|---|---|
| EP | 0 263 657 A3 | 10/1987 |
| EP | 0 263 657 | 4/1988 |
| EP | 0 730 868 A1 | 2/1996 |
| WO | WO 86/01805 | 3/1986 |
| WO | WO 86/01806 | 3/1986 |
| WO | WO 91/01305 | 2/1991 |
| WO | WO 97/08553 | 3/1997 |

OTHER PUBLICATIONS

Sleight et al. Signal Transduction. In: Cell Physiology Source Book. N. Sperelankis (ed). 1995.*
Karube et al. Current Opinion in Biotechnology 5(1):54-59, 1994.*
Sleight et al. Signal Translation. In: Cell Physiology Source Book. N. Sperelankis (ed). 1995.*
Miller et al. Proc. Natl Acad. Sci 86:5054-5058, 1989.*
Garcia Vescovi et al. Cell 84:165-174, 1996.*
Walsh, Enzymatic Reaction Mechanisms, W.H. Freeman and Company, 1979 p. 185.*
Alfano, R.R., et al., 1987, "Flourescence Spectra from Cancerous and Normal Human Breast and Lung Tissues," IEEE *Journal of Quantum Electronics* QE-23 (10): 1806-1811.
Alfano, R.R., et al., 1991, "Light Sheds Light on Cancer-Distinguishing Malignant Tumors from Benign Tissues and Tumors," *Bull N.Y. Acad. Med.* 37 (2):143-150.
Araki, Kazuo, 1995, "Photo-detection of transferred gene expression in fish," *Chemical Abstracts* 123: Abstract No. 189418.
Casedi, J., et al., 1990, "Expression and Secretion of Aequorin as a Chimeric Antibody by Means of a Mammalian Expression Vector," *Proc. Natl. Acad. Sci. USA* 87:2047-2051.
Chalfie, M. et al., 1994, "Green *Flourescent Protein as a Marker for Gene Expression," *Science* 263:802-805.
Contag et al., 1994, "Optical tracking of Infection In Vivo Using Light-Generating Probes," *Pediatric Research* 37:172A.
Hooper, C.E., et aL, CCD Imaging of Luciferase Gene Expression in Single Mammalian Cells, "journal of Bioluminescence and Chemiluminescence," 5:123-130.
Horan, et aL, 1990, "Flourescent Cell Labeling for In Vivo and In Vitro cell tracking," *Methods in Cell Biology* 33:469-490.
Korpela, M. et al., "Stable light emitting *Escherichia coli* as a Biosensor," *Journal of Bioluminescence and Chemiluminescence* 4: 551-554.
Kuhn et al., 1991 *Arch Surg.* 126:1398-1403.
Mackay et al., 1994, "Thermostability of bacterial luciferase expressed in different microbes," *J. Appl. Bacteriol* 77: 149-54 (Will Be Sent Under Separate Cover).
Mayer et al., 1994, "Luminescent Labels-More than just an Alternative to Radioisotopes?," *Angewandte Chemie International Edition* 33:1044-10-22.
Meighen, E.A., 1993, "Bacterial Bioluminescence: Organization, Regulation and Application of the *lux* Genes," *The FASEB Journal* 7:1016-1022.
Mueller-Kliesser and Walenta, 1993, "Geographical Mapping of Metabolites in Biological Tissue with Quantitative Bioluminescence and Single Photon Imaging," *Histochemical Journal* 25:407-420.
Schaefer, C. et al., 1992, "Oxygentaion and Bioenergetic Status of Murine Fibrosarcomas," *Oxygen Transport to Tissue XIV* (Erdman, W. and D.F. Bruley, eds., Plenum Press, New York: 161-166.
Tamiya, et al., 1990, "Spatial Imaging of Luciferase Gene Expression in Transgenic Fish," *Nucleic Acids Research* 18(4):1072.
Tang, et al., 1989, "Spectroscopic Difference between Human Cancer and Normal Lung and Breast Tissues," *Lasers in Surgery and Medicine* 9:290-295.
Wood, et al., 1989, "Complemntary DNA Coding Click Beetle Luciferases Can Elicit Bioluminescence of Different Colors," *Science* 244:700-702.
Zhang, et al., 1994, "Luciferase Activity as a Marker of Tumor Burden and as an indicator of Tumor Response to Antineoplastic Therapy in vivo," *Clinc. Exp. Metastasis* 12:87-92.

(Continued)

*Primary Examiner* — Robert A Zeman
(74) *Attorney, Agent, or Firm* — Pasternak Patent Law; Dahna S. Pasternak

(57) ABSTRACT

The present invention relates to biodetectors for detecting and quantifying molecules in liquid, gas, or matrices. More specifically, the present invention relates to biodetectors comprising a molecular switching mechanism to express a reporter gene upon interaction with target substances. The invention further relates to methods using such biodetectors for detecting and quantifying selected substances with high specificity and high sensitivity.

9 Claims, 5 Drawing Sheets

OTHER PUBLICATIONS

Blom, et al., 1993 "A Baculovirus-Expressed Fusion Protein Containing the Antibody-Binding Domain of Protein A and Insect Luciferase." *BioTechniques* 14(5):800-809.
Brennan, et al., 1995 "A Molecular Sensor System Based on Genetically Engineered Alkaline Phosphatase." *Proc. Natl. Acad. Sci. USA* 92:5783-5787.
Borrebaeck et al., 1992 "Kinetic analysis of Recombinant Antibody-Antigen Interactions: Relation Between Structural Domains and Antigen Binding." *Biotechnology* 10(6):697-698.
Brasier, et al.. 1992 "Luciferase Reporter Gene Assay in Mammalian Cells." *Methods. in Enzymology* 216:386-396.
Candido, et al., 1996 "Transgenic *Caenorhabditis elegans* strains as biosensors." *Trends in Biotechnology* 14:125-129.
Contag, et al., 1997 "Visualizing Gene Expression in Living Mammals Using a Bioluminescent Reporter." *Photochemistry and Photobiology* 66(4):523-531.
Contag, et al., 1995 "Photonic detection of bacterial pathogens in living hosts." *Molecular Microbiol ogy* 18(4):593-603.
DiLella, et al., 1988 "Utility of firefly luciferase as a reporter gene for promoter activity in transgenic mice." *Nucleic Acids Research* 16(9):4159.
Enberg, B., et al. 1994 "Growth hormone (GM) regulation of a rat serine protease inhibitor fusion gene in cells transfected with GH receptor cDNA." *Journal of Molecular Endocrinology* 12:39-46.
Frackman, et al., 1990 "Cloning, Organization, and Expression of the Bioluminescence Genes of *Xenorhabdus luminescens*." *Journal of Bacteriology* 172(10):5767-5773.
Griffiths et al., 1998 "Strategies for selection of antibodies by phage display." *Current Opinion in Biotechnology* 9:102-108.
Hannibal, et al. 1994 "Multiple cis-acting elements in the human immunodeficiancy virus type 2 enhancer mediate the response to T-cell receptor stimulation by antigetn ina T-cell hybridoma line." *Blood* 83(7):18391846.
Hasemann, et al., 1989 "Immunoglobulins: Structure and Function", *In Fundamental Immunology 2nd (Ed.)* W.E. Paul:209-233.
Hoogenboom, et al., 1991 "Multi-subunit proteins on the surface of filamentous phage: methodologies for displaying antibody (Fab) heavy and light chains." *Nucleic Acids Research* 19(15):4133-4137.
Hooper et al., 1994 "Low-Light Imaging Technology in the Life Sciences." Journal of Bioluminescence and Chemiluminescence 9:113-122.
Huse et al., 1989 "Generation of a Large Combinatorial Library of the Immunoglobulin Repertorie in Phage Lambda." *Science* 246:1275-1281.
Israel, et al., 1991 "Bioluminescence assay for gene expression by continuously growing mammalian cells: application for detection of human immunodeficiency virus type 1 (HIV-1)." *Gene* 104:139-145.
Karube, et al., 1994, "Immobilized cells used for detection and analysis" *Curr. Opin. Biotechnol.* 5(1):54-59.
Kasahara, et al., 1991 "Molecular analysis of the *Salmonella typhimurium* phoN gene, which encodes nonspecific acid phosphatase." *Journal of Bacteriology* 173(2):6760-6765.
Kasahara, et al., 1992 "Molecular analysis of the *Esherichia coli* phoP-phoQ operon." Journal of Bacteriology 174(2):492-498.
Kohl et al., 1990, "Engineered gene for *Escherichia coli* alkaline phosphatase for the construction of translational fusions." *Nucleic Acids Res.* 18:1069.
Kohl, et al., 1991 "Cloning and Expression of an HIV-1 Specific Single-Chain F. Region Fused to *Escherichia coli* Alkaline Phosphatase." *Ann NY Acad Sci.* 646:106-114.
Kovacs, et al., 1991 "Firefly luciferase as a marker for herpesvirus (*pseudorabies virus*) replication in vitro and in vivo" *J. Gen. Virol.* 72:2999-3008.
McCafferty, et al., 1990 "Phage antibodies: filamentous phage displaying antibody variable domains." *Nature* 348:552-554.
Miller, et al., 1989 "A two-component regulatory system (phoP phoQ) controls *Salmonella typhimurium* virulence." *Proc. Natl. Acad. Sci. USA* 86:5054-5058.
Miller, S.I., 1991 "PhoP/PhoQ: macrophage-specific modulators of *Salmonella* virulence?" *Molecular Microbiology* 5(9):2073-2076.
Mueller-Klieser, et al., 1993 "Geographical Mapping of Metabolites in biological tissue with quantitative bioluminescence and single photon imaging." *Institute of Physiology & Pathophysiology* Nov. 16, 1992 and in revised from Jan. 23, 1993.
Orum, et al., 1993 "Efficient method for constructing comprehensive murine Fab antibody libraries displayed on phage." *Nucleic Acids Res* 21:4491-4498.
Ottemann, et al., 1993 "Converting a transmembrane receptor to a soluble receptor: recognition domain to effector domain signaling after excision of the transmembrane domain." *Proc. Natl. Acad. Sci . USA* 94:11201-11204.
Parkinson, J.S., 1993 "Signal Transduction Schemes of Bacteria." *Cell* 73:857-871.
Ramanathan, et al., 1997 "Bacterial biosensors for monitoring toxic metals." *Trends Biotechnol* 15:500-506.
Ronald et al., 1990, " Construction of broad-host-range for the selection of divergent promoters." *Gene* 90:145-148.
Rupani, et al., 1996 "Characterization of the Stress Response of a Bioluminescent Biological Sensor in Batch and Continuous Cultures." *Biotechnol. Prog.* 12:387-392.
Soncini, et al., 1995 "Transcriptional autoregulation of the *Salmonella typhimurium* phoPQ operon." *Journal of Bacteriology* 177(15):4364-4371.
Soncini, et al., 1996 "Molecular basis of the magnesium deprivation response in *Salmonella typhimurium*: identification of PhoP-regulated genes." *Journal of Bacteriology* 178(17):5092-5099.
Swift, et al., 1994 "Gram-negative bacterial communication by *N-acyl* homoserine lactones: a universal language?." *Trends in Microbiology* 193:2(6):193-198.
Szittner, et al., 1990 "Nucleotide Sequence, Expression, and Properties of Luciferase Coded by lûx genes from a Terrestrail Bacterium." *J. Biol. Chem.* 265:16581-16587.
Van Dyk, et. al. 1994 "Rapid and sensitive pollutant detection by induction of heat shock gene-bioluminescen gene fusion's." *Applied and Environmental Microbiology* 60(5):1414-1420.
Weiss, et al., 1994 "Application of an alkaline phosphatase fusion protein system suitable for efficient screening and production of Fab-enzyme conjugates in *Escherichia coli*" *J. Biotechnol.* 33:43-53.
Vescovi, et al., 1996 "Mg2+ as an Extracellular signal: environmental regulation of *Salmonella* virulence." *Cell* 84:165-174.
Willardson, et al., 1998 "Development and Testing of a Bacterial Biosensor for Toluene-Based Environmental Contaminants." *Applied and Environmental Microbiol ogy* 64(3):1006-1012.
Wood, et al., 1996 "Transduction in microbial biosensors using multiplexed bioluminescene." *Biosensors & Bioelectronics* vol. 11(3):207-214.
Xi et al., 1991, "Cloning and Nucleotide Sequences of lux Genes and Characterization of Luciferase of *Xenorhabdus luminescens* from a Human Wound." *J. Bact.* 173:1399-1405.
Blum, et al. 1989 "Design of luminescence photobiosensors." *Journal of Bioluminescence and Chemilumenscence* 4:543-550.
Danilov, et al. 1989 "Bacterial Luciferase as a Biosensor of Biologically Active Compounds." *Biotechnology* 11:39-78.
Kobatake, et al., 1995 "Biosensing of benzene derivatives in the environment by luminescent *Escherichia coli*" *Biosensors & Bioelectronics* 10:601-605.
Kubo, et al. 1991 "Whole-Organism Based Biosensors and Microbiosensors." *Advances in Biosensors* 1:1-32.
Sedlack, et al 1995 "Bioluminescent Technology for Reagents, Diagnostics and Toxicology." Genetic Engineering News *Genetic Engineering News* 8 (Sep. 15, 1995).
Wilmes-Riesenberg, et al. 1992 "TnphoA and TnphoA elements for making and switching fusions for study of transcription, translation, and cell surface localization." *J. Bacteriol* 174:4558-75.
Collet, T.A., et al. 1992 "A binary plasmid system for shuffling combinatorial antibody libraries." *Proc. Natl. Acad. Sci. USA* 89:10026-10030.
Francisco, J.A., et al. 1994 "The Expression of Recombinant Proteins on the External Surface of *Escherichia coli*." *Ann. N.Y. Acad. Sci.* 745:372-382.
Fuchs, et al. 1991 Targeting Recombinant Antibodies to the Surface of *Escherichia coli*: Fusion to a Peptidoglycan Associated Lipoprotein. *Bio/Technology* 9:1369-1372.
Georgiou, G., et al. 1993 "Practical applications of engineering Gram-negative bacterial cell surfaces." *TIBTECH* 11:6-10.

Georgiou, G., et al. 1997 "Display of heterologous proteins on the surface of microorganisms: From the screening of combinatorial libraries to live recombinant vaccines." *Nature Biotechnology* 15:29-34.

Little, M., et al. 1993 "Bacterial surface presentation of proteins and peptides: an alternative to phage technology?" *TIBTECH* 11:3-5.

Little, M., et al. 1995 "Human antibody libraries in *Escherichia coli.*" *Journal of Biotechnolgy* 41:187-195.

Stahl, S., et al. 1997 "Bacterial surface display:trends and progress." *TIBTECH* 15:185-192.

Askin, "Bacterial and Fungal Infections in the Neonate," *Journal of Obstetric, Gynecologic, Neonatal Nurses*, 24:635-643 (1995).

Benaron, et al., "Optical Time-of-Flight and Absorbance Imaging of Biologic Media," *Science*, 259:1463-1466 (1993).

Benaron, et al., "Medical Optical Tomography: Functional Imaging and Monitoring," *Spie Optical Engineering Press*, pp. 3-9 (1993).

Benaron, et al., "Resolution of Near Infrared Time-of-flight Brain oxygenation Imaging," *Advances in Experimental Medicine and Biology*, 345:609-617 (1994).

Clark, et al., "Unsuspected Primary Human Immunodficiency Virus Type 1 Infection in Seronegative Emergency Department Patients," *The Journal of Infectious Diseases*, 170:194-197 (1994).

Guzzo, et al., "Characterization fo the Effects of Aluminum on Luciferase Biosensors for the Detection of Ecotoxicity," *Toxicology Letters*, 64/65:687-693 (1992).

Harlow, et al., "Antibodies. A Laboratory Manual," *Cold Spring Harbor Laboratory Press*, (1988).

Heitzer, et al., "Optical Biosensor for Environmental On-Line Monitoring of Naphthalene and Salicylate Bioavailability With an Immobilized Bioluminescent Catabolic Reporter Bacterium," *Applied and Environmental Microbiology*, 60(5):1487-1494 (1994).

Hickey, et al., "Luciferase In Vivo Expression Technology: Use of Recombinant Mycobacterial Reporter Strains to Evaluate Antimycobacterial Activity in Mice," *Antimicrobial Agents and Chemotherapy*, 40(2): 400-407 (1996).

Hooper, et al., "Low-Light Imaging Technology in the Life Sciences," *J. Biolumin Chemilumin*, 9:113-122 (1994).

Jassim, et al., "In vivo Bioluminescence: A Cellular Reporter for Reseach and Industry," *Journal of Bioluminescence and Chemiluminescence*, 5:115-122 (1990).

Kricka, "Chemiluminescent and Bioluminescent Techniques," *Clinical Chemistry*, 37(9):1472-1481 (1991).

Phadke, "Biosensors and Enzyme Immobilized Electrodes," *BioSystems*, 27:203-206 (1992).

Piatak, Jr., et al., "Determination of Plasma Viral Load in HIV-1 Infection by quantitative Competitive Polymerase Chain Reaction," *Aids Supplemental*, 7(3):S65-S71 (1993).

Selifonova, et al., "Bioluminescent Sensors for Detection of Bioavailable Hg(II) in the Environment," *Applied and Environmental Microbiology*, 59(9):3083-3090 (1993).

Tatsu, et al., "Homogeneous chemiluminescent Immunoassay Based on Complement-Mediated Hemolysis of Red Blood Cells," *Analytical Chemistry*, 62:2103-2106 (1990); and.

von Bally, et al., Optics in Biomedical Sciences: Proceedings of the International Conference (Berlin, New York: Springer-Verlag).

Guzzo, et al., "Characterization fo the Effects of Aluminum on Luciferase Biosensors for the Detection of Ecotoxicity," *Toxicology Letters*, 64 /65:687-693 (1992).

Tatsu, et al., "Homogeneous chemiluminescent Immunoassay Based on Complement-Mediated Hemolysis of Red Blood Cells," *Analytical Chemistry*, 62:2103-2106 (1990).

von Bally, et al., Optics in Biomedical Sciences: Proceedings of the International Conference (Berlin, New York: Springer-Verlag.

\* cited by examiner

A. In the presence of ligand ($Amp^r$, $Kan^r$, $Chl^s$ and bioluminescent).

B. In the absence of ligand ($Amp^r$, $Chl^r$, $Kan^s$ and <u>NOT</u> bioluminescent)

BIODETECTORS TARGETED TO SPECIFIC LIGANDS

This application claims the benefit of U.S. Provisional Application No. 60/015,633, filed Apr. 19, 1996.

I. FIELD OF THE INVENTION

The present invention relates to biodetectors for detecting and quantifying molecules in liquid, gas, or on solid matrices. More specifically, the present invention relates to biodetectors comprising a molecular switching mechanism to express a reporter gene upon interaction with target substances. The invention further relates to methods using such biodetectors for detecting and quantifying selected substances with high specificity and high sensitivity.

II. BACKGROUND OF THE INVENTION

The detection of low-levels of biological and inorganic materials in biological samples, in the body or the environment is frequently difficult. Assays for this type of detection involve multiple steps which can include binding of a primary antibody, several wash steps, binding of a second antibody, additional wash steps, and depending on the detection system, additional enzymatic and washing steps. Such assays further suffer from lack of sensitivity and are subject to inaccuracies. For instance, traditional immunoassays miss detecting 30% of infections.

Molecular probe assays, although sensitive, require highly skilled personnel and knowledge of the nucleic acid sequence of the organism. Both the use of nucleic acid probes and assays based on the polymerase chain reaction (PCR) can only detect nucleic acid which require complicated extraction procedures and may or may not be the primary indicator of a disease state or contaminant. Both types of assay formats are limited in their repertoire in cases where little information is available for the entity to be detected.

Current noninvasive means to measure a patients physical parameters such as CAT or MRI, are expensive and are often inaccessible. Thus, the monitoring of many medical problems still requires tests, which can be slow and expensive. The time between the actual test and the confirmation of the condition may be very important. For example, in the case of sepsis, many patients succumb before infection is confirmed and the infecting organism identified, thus treatment tends to be empirical and less effective. Another example is in screening the blood supply for pathogens.

Verification of a pathogen free blood supply requires a number of labor intensive assays. In the case of HIV-1, the virus that causes AIDS, the current assays screen for anti-HIV antibodies and not the virus itself. There is a window lasting up to many weeks after exposure to the virus in which antibodies are not detectable, and yet the blood contains large amounts of infectious virus particles. Clark et al., 1994, *J. Infect. Dis.* 170:194-197; Piatak et al., 1993, *Aids Suppl.* 2: S65-71.

For example, in order to verify that a blood supply is free of HIV-1, several labor-intensive, expensive tests must be performed. Moreover, tests currently in use for initial screening do not identify the virus itself, which can be present at relatively low levels, but are directed to HIV antibodies which are not present for weeks after an initial infection. Clark et al., 1994, *J. Infect. Dis.* 170:194-197; Piatak et al., 1993, *Aids Suppl.* 2:S65-71. Thus, screening of the blood supply is not only time-consuming and slow, it may also be inaccurate.

Similarly, the ability to detect substances in the environment, such as airborne and waterborne contaminants is of great importance. For example, it would be desirable to monitor groundwater, to control industrial processes, food processing and handling in real-time using an inexpensive versatile assay. However, current methods) are not suited for such "on-line" monitoring.

There are several reasons why current methods are limited. First, access to sufficient amounts of the material to be detected may be difficult. For example, the detection of biological materials can be difficult as the biological materials of interest are often sequestered inside a body, and large quantities can be difficult to obtain for ex vivo monitoring. Therefore, sensitive assays for use on small amounts of material are necessary. This indicates that a method of amplifying the signal is required. Amplification methods have been established for detection of nucleic acid but this is not the case for antigen detection methods.

A second problem is that sensing may be difficult in real-time because the target materials may be present in small quantities that detection of their presence requires time-consuming, expensive and technical by-involved processes. For example, in the case of bacterial infections in the blood, sepsis, there may be only 1-2 bacteria in a 1-10 ml blood sample. Current methods require that the bacteria are grown first in order to be detected. Askin, 1995, *J. Obstet. Gynecol. Neonatal. Nurs.* 24:635-643. This time-lag may be detrimental as delaying treatment or mistreating diseases may mean the difference between life and death.

Others have attempted to avoid these limitations by using radioactive or fluorescent tags in combination with antibodies (Harlow et al., (1988), *Antibodies. A Laboratory Manual* (Cold Spring Harbor, N.Y.: Cold Spring Harbor Laboratory Press). Antibody-based assays typically involve binding of an antibody to the target molecule, followed by a series of washing steps to remove all unbound antibodies. Binding of the antibody to its target molecule is typically detected by an identifier molecule, for example a secondary antibody specifically recognizing the target molecule specific antibody which contains a detectable label. The step is also followed by multiple wash steps. Alternatively, the target-specific antibody may directly be attached to a detectable label. Labels have included radioactive tracers, fluorescent tags, and chemiluminescent detection systems. Harlow and Lane, 1988, *Antibodies. A Laboratory Manual* (Cold Spring Harbor, N.Y.: Cold Spring Harbor Laboratory Press).

The series of steps required using such antibody-based assays to generate a specific signal are time consuming and labor intensive. Furthermore, these type of assays are limited to the detection of antigens fixed to some type of matrix. Examples of this type of detection system include Western blots, immunohistochemistry, and ELISA. The highest sensitivity is currently being achieved using radioisotopic and chemiluminescent tags. However, sensitivity, i.e., specific signal over background, of these detection systems frequently remains a limiting factor.

Similarly, background radiation places limits on the sensitivity of radioactive immunoassay techniques. In addition, these techniques are time-consuming and expensive. Finally, radioactive approaches are hostile to the environment, as they present significant waste disposal problems.

Another approach to monitoring substances involves the use of light. Light has the advantage that it is easily measurable, noninvasive and quantitative. Von Bally a al., (1982), *Optics in Biomedical Sciences: Proceedings of the International Conference* (Berlin, N.Y.: Springer-Verlag).

Traditional spectroscopy involves shining light into substances and calculating concentration based upon the absorbance or scattering of light. Von Bally et al., (1982), *Optics in Biomedical Sciences: Proceedings of the International Conference* (Berlin, N.Y.: Springer-Verlag). Optical techniques detect variations in the concentration of light-absorbing or light scattering materials. Von Bally a al., (1982), *Optics in Biomedical Sciences: Proceedings of the International Conference* (Berlin, N.Y.: Springer-Verlag). Near-infrared spectroscopy has proved to be a nonionizing, relatively safe form of radiation that functions well as a medical probe as it can penetrate into tissues. Further, it is well-tolerated in even large dosages. For example, light is now used to calculate the concentration of oxygen in the blood (Nelicor) or body (Benaron image), or even to monitor glucose in the body (Sandia). Benaron and Stevenson, 1993, *Science* 259:1463-1466; Benaron et al., 1993, in: *Medical Optical Tomography: Functional Imaging and Monitoring*, G. Muller, B. Chance, R. Alfano and e. al., eds. (Bellingham, Wash. USA: SPIE Press), pp. 3-9; Benaron and Stevenson, 1994, *Adv. Exp. Med. Biol.* 361:609-617. However, current techniques are limited in that many substances do not have unique spectroscopic signals which can be optically assessed easily and quantitatively. Von Bally et al., (1982), *Optics in Biomedical Sciences: Proceedings of the International Conference* (Berlin, N.Y.: Springer-Verlag). Furthermore, the detection of substances at low concentration is frequently hampered by high background signals, especially in biological media such as tissues. Von Bally et al., (1982), *Optics in Biomedical Sciences: Proceedings of the International Conference* (Berlin, N.Y.: Springer-Verlag).

Over the past years, assays based on light emission, for example chemiluminescence (Tatsu and Yoshikawa, 1990, *Anal. Chem.* 62:2103-2106), have attracted increasing attention due to the development of extremely sensitive methods for detecting and quantifying light. Hooper et al., 1994, *J. Biolumin. Chemilumin.* 9:113-122. One example of a biomedical research product using chemiluminescence is the ECL detection system (Amersham) for immunoassays and nucleic acid detection.

The use of biological sources of light, bioluminescence, for biological assays has paralleled development of chemiluminescent detection, as similar devices for light detection are required. Kricka, 1991, *Clin. Chem.* 37:1472-1481. One of the most commonly employed biological source of light is luciferase, a light-generating enzyme synthesized by a range of organisms, including *Photinus pyralis* (American firefly), *Renilla reniformis* (phosphorescent coral), and *Photobacterium* (Luminescent bacterial species). Generally, luciferase is a low molecular weight oxidoreductase, which catalyzes the dehydrogenation of luciferin in the presence of oxygen, ATP and magnesium ions. During this process, about 96% of the energy released appears as visible light. For review, see, Jassim et al., 1990, *J. Biolumin. Chemilumin.* 5:115-122.

The sensitivity of photon detection and the ability to engineer bacteria and other cells to express bioluminescent proteins permit the use of such cells as sensitive biosensors in environmental studies. Guzzo et al., 1992, *Toxicol. Lett.* 64:687-693; Heitzer et al., 1994, *Appl. Environ. Microbiol.* 60:1487-1494; Karube and Nakanishi, 1994, *Curr. Opin. Biotechnol.* 5:54-59; Phadke, 1992, *Biosystems* 27:203-206; Selifonova et al., 1993, *Appl. Environ. Microbiol.* 59:3083-3090. For example, Selifonova et al. describe biosensors for the detection of pollutants in the environment. More specifically, using fusions of the Hg(II) inducible Tn21 operon with the promoterless luxCDABE from *Vibrio fischeri*, highly sensitive biosensors for the detection of Hg (II) have been constructed.

In addition to systems where bioluminescence is used as detection method of a specific condition, e.g., the presence of Hg(II), supra, constitutive expression of luciferase has been employed as marker to track viability of bacterial cells, as the luciferase assay is dependent on cell viability. For example, constitutive expression of luciferase has recently been employed for the development of drugs and vaccines directed against bacterial disease. Specifically, using an enhanced luciferase-expressing *Mycobacterium tuberculosis* strain has been employed to evaluate antimicrobacterial activity in mice. Hickey et al., 1996, *Antibacterial Agents and Chemotherapy* 40:400-407.

However, biosensors that rely on a bacterial receptor to film on a luciferase are limited to sensing those molecules that are have a corresponding bacterial receptor, linked to a known promoter region which can be fused to the luciferase gene. Further, the luciferase-expressing bacteria used to test antimicrobial activity in mice are nonspecific.

Thus, while methods have been explored using the bioluminescence in general, and luciferase in particular, as bioluminescent sensors for very specific applications, the present invention is directed to highly sensitive and highly selective ligand-specific biodetectors for a very broad range of applications. More specifically, the present invention combines the selectivity of ligand-specific binding and the versatility of the antibody repertoire with the sensitivity of bioluminescent detection, employing entities that specifically respond with photon emission to predetermined ligands. The approach of the present invention thus permits the generation of extremely sensitive biodetectors for the development of a wide variety of assays detecting any number of commercially important molecules.

III. SUMMARY OF THE INVENTION

The present invention is directed to targeted ligand-specific biodetectors for detecting and monitoring selected substances. More specifically, the biodetectors of the present invention comprise (1) a signal converting element, comprising an extracellular ligand-specific binding moiety, which is fused to an intracellular signal transforming domain which is capable of activating a (2) transducer component, which in its active form is capable of activating a (3) responsive element, such as a promoter which is operatively linked to a (4) reporter gene, encoding for a polypeptide with unique properties that are easily detected, for example optically. Thus, the biodetectors of the invention convert the binding to a target substance, i.e., a ligand, into a detectable signal. In preferred embodiments of the invention, the signal generated by the biodetector is light and is detected by a light-detecting device. Accordingly, a substance of interest may be identified.

The present invention is further directed to methods using such biodetectors for detecting and monitoring selected substances at high sensitivity and high specificity. The methods using the biodetectors of the invention include the detection of contaminants in the food and agriculture industry, diagnosis and monitoring in medicine and research, and detection of poisons or contaminants in the environmental or defense setting.

IV. BRIEF DESCRIPTION OF THE FIGURES

Figure 4:
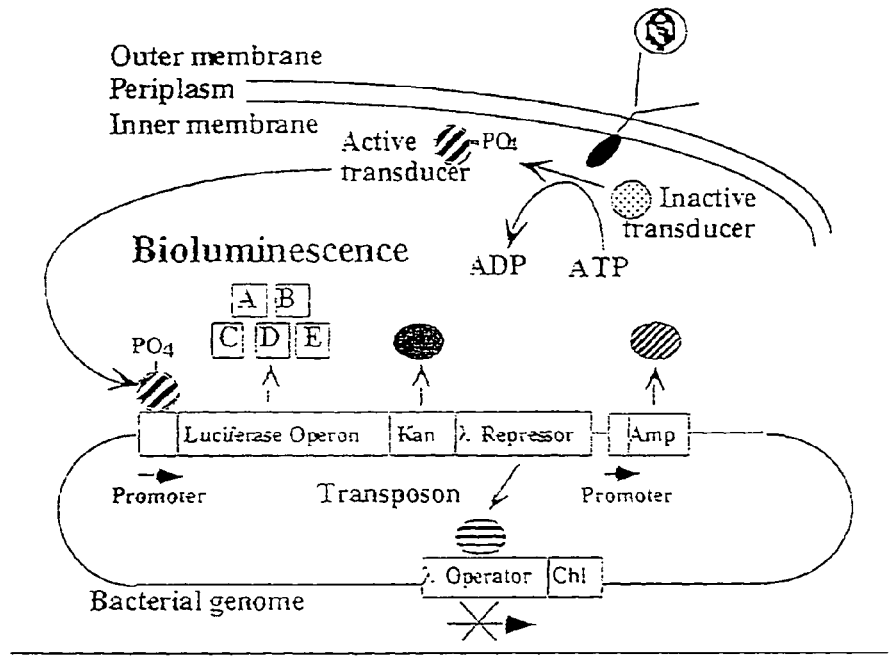
Figure 4:
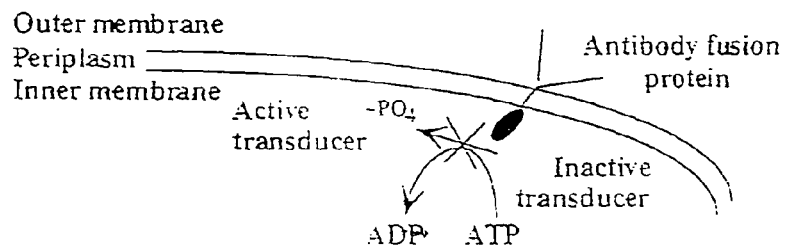

FIG. 4 depicts a biodetector generated by the integration of a transposon in the bacterial genome as specified in EXAMPLE 1. The luciferase operon encodes five proteins (from genes A, B, C, D and E) that together can produce bioluminescence. Ch1, chloramphenicol resistance gene; Kan, kanamycin resistance gene; Amp, Ampicillin resistance gene; $PO_4$, phosphate group (as activator of the transducer).

Figure 5:
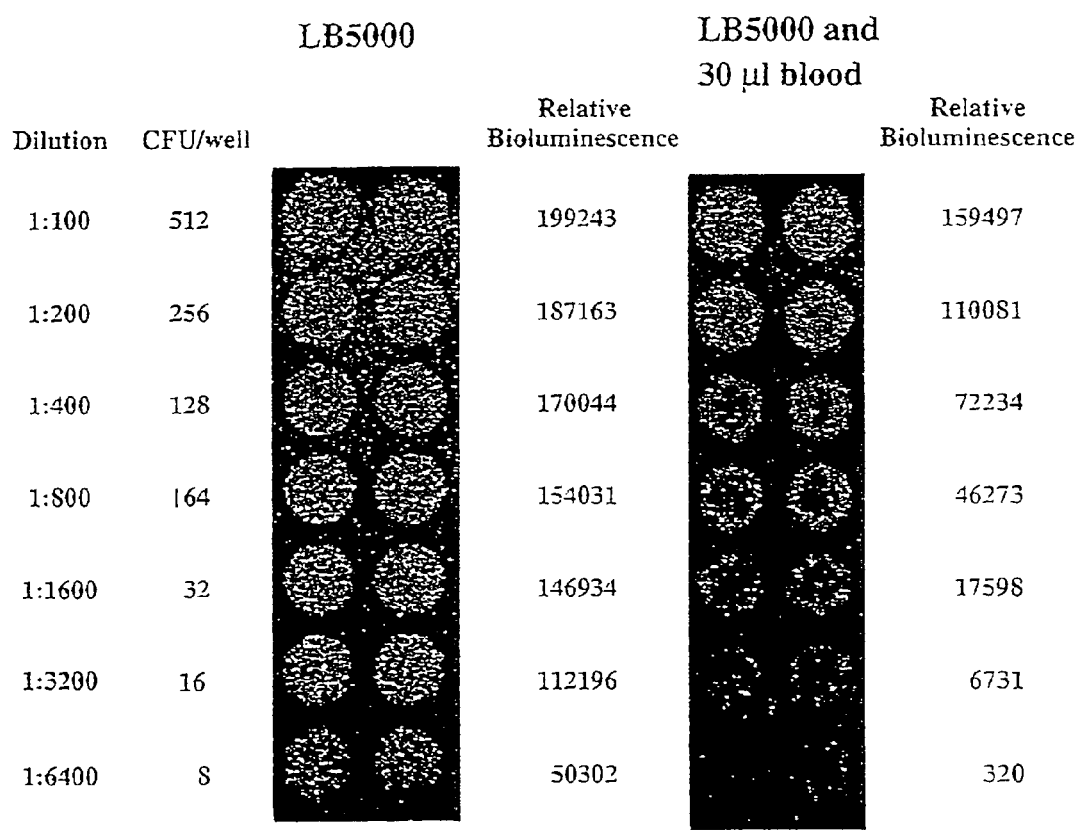

FIG. 5 depicts the effect of human blood on the light emission from bioluminescent *Salmonella*, demonstrating near single cell detection.

V. DEFINITIONS

Unless otherwise indicated, all terms used herein have the same meaning as they would be understood by one skilled in the art.

The term "target molecule" as used herein describes a substance that is to be detected and/or quantified.

The term "luciferases" as used herein, unless otherwise stated, includes prokaryotic and eukaryotic luciferases as well as variants with varied or altered physical and/or emission properties.

The term "biodetector" as used herein refers to an entity that responds with an optical signal to the binding or otherwise interacting with the target molecule.

The term "optical signal" as used herein refers to any biochemical reaction or substance that can be distinguished using light monitoring techniques. This includes photon emission, fluorescence, and absorbance.

The term "light" as used herein, unless otherwise stated, refers to electromagnetic radiation having a wavelength between about 220 nm and about 1100 nm.

The term "promoter induction" as used herein refers to an event that results in direct or indirect activation of a selected inducible genetic element.

VI. DETAILED DESCRIPTION OF THE INVENTION

A. General Overview of the Invention

The present invention is directed to targeted ligand-specific biodetectors for detecting and monitoring selected substances, including microorganisms, molecules, and ions, for a wide range of applications. The biodetectors of the present invention combine the specificity and selectivity of ligand-specific binding with the sensitivity of bioluminescent detection by employing entities that specifically respond to the binding of a predetermined ligand with photon emission. Thus, the approach of the present invention permits the generation of sensitive biodetectors for the development of a wide variety of assays detecting and monitoring any selected substance.

More specifically, the biodetectors of the present invention provide for the coupling of ligand-specific binding, via a "molecular switch", i.e., a signal transduction, with the activation of a detectable reporter molecule in response to ligand binding. The biodetectors of the present invention may consist of viable biological entities, such as bacteria, or abiotic entities, such as liposomes. As general scheme, the biodetectors are characterized by their ability to specifically recognize a ligand and convert binding to the ligand to a measurable signal, such as light emission. For example, bacteria may be employed as ligand-specific biodetectors, which specifically respond with photon emission to predetermined ligands.

The biodetectors of the present invention permit highly sensitive detection of a wide variety of substances, for example microbes in human blood, viruses and bacteria, toxic molecules, ions, cancer cells, antigens, small molecules (e.g., glucose), pH, oxygen, and metals. Further, the present invention provides for the use of such biodetectors in a wide variety of assays to detect any selected substance.

Generally, the biodetectors of the present invention comprise a signal converting element, comprising an extracellular ligand-specific binding moiety, which is coupled to an intracellular signal transforming domain which is capable of activating a transducer component. The transducer component in its active form is capable of activating a responsive element, such as a promoter which is operatively linked to a reporter gene, encoding for a diagnostic polypeptide with unique properties that are readily detectable. In the alternative, a reporter molecule is activated directly by binding other intracellular signal transforming domain of the signal converting element. Thus, the biodetectors of the invention convert the binding to a target substance, i.e., a ligand, into a detectable signal. In preferred embodiments of the invention, the signal generated by the biodetector is light and is detected by a light-detecting device. Accordingly, based upon this interaction, the targeted ligand(s) may be quantified and identified.

B. Biodetectors

The biodetectors of the invention are characterized in that they generate a detectable signal in response to either the presence of a targeted substance in vivo or in vitro.

In one specific embodiment, light is the detectable signal generated by the biodetector in response to the presence of the targeted substance. As there is virtually no background light coming from normal tissues and other organic or inorganic materials, the sensitivity of the system is limited only by the background noise of the biodetector. More specifically, the targeted ligand-specific biodetectors of the present invention consist of a ligand-specific domain, which, via a "molecular switch", is linked to a reporter gene encoding a detectable protein. The reporter gene is thus activated in response to binding of the ligand to the ligand-specific domain. The ligand-specific binding moiety may be any antibody which selectively binds to the substance of interest. The "molecular switch" is a signal transducing component which couples ligand binding to the activation of a responsive element. The transducing molecule can be any two component regulatory system of bacteria, including phosphate regulon, or any eukaryotic transducer. The responsive element may be an inducible promoter, operatively linked to a reporter gene. Transcription and translation of this reporter gene will result in a gene product which produces a detectable signal, such as light. The signal is detected by suitable means; in the case the signal is light, this means will be a photodetection device.

For example, imaging of the light-emitting biodetector entities may involve the use of a photodetector capable of detecting extremely low levels of light—typically single photon events. If necessary, localization of signal could be determined by integrating photon emission until an image can be constructed. Examples of such sensitive photodetectors include devices (such as microchannelplate intensifiers and photomultiplier tubes) that intensify the single photon events. Intensifiers may be placed before a camera. In addition, sensitive cameras (cooled, for example, with liquid nitrogen) that are capable of detecting single photons over the background noise inherent in a detection system may also be used.

Once a photon emission image is generated, it is typically superimposed on a "normal" reflected light image of the subject to provide a frame of reference for the source of the emitted photons. Such a "composite" image is then analyzed to determine the location and/or amount of a target in the subject. In most circumstances images of the light source are not required. Simple quantitation of the numbers of photons emitted from a sample (as detected for example by a luminometer) indicate the concentration of the light emitting reporter. The number of photons would therefore be proportional to the amount of targeted-ligand that a specific detector is sensing. Without the constraints imposed by the need for an image, detectors can be placed in very close proximity to the light-emitting biodetector thus optimizing the optical detection and sensitivity of the assay. Microchannel plate intensifiers can be used in such a configuration resulting in single photon detection. Such a device is currently manufactured by Hamamatsu Corporation. In the Hamamatsu system ATP concentrations from single cells can be assayed by spraying lysis buffer, luciferase and the substrate, luciferin, on immobilized cells.

Figure 1:
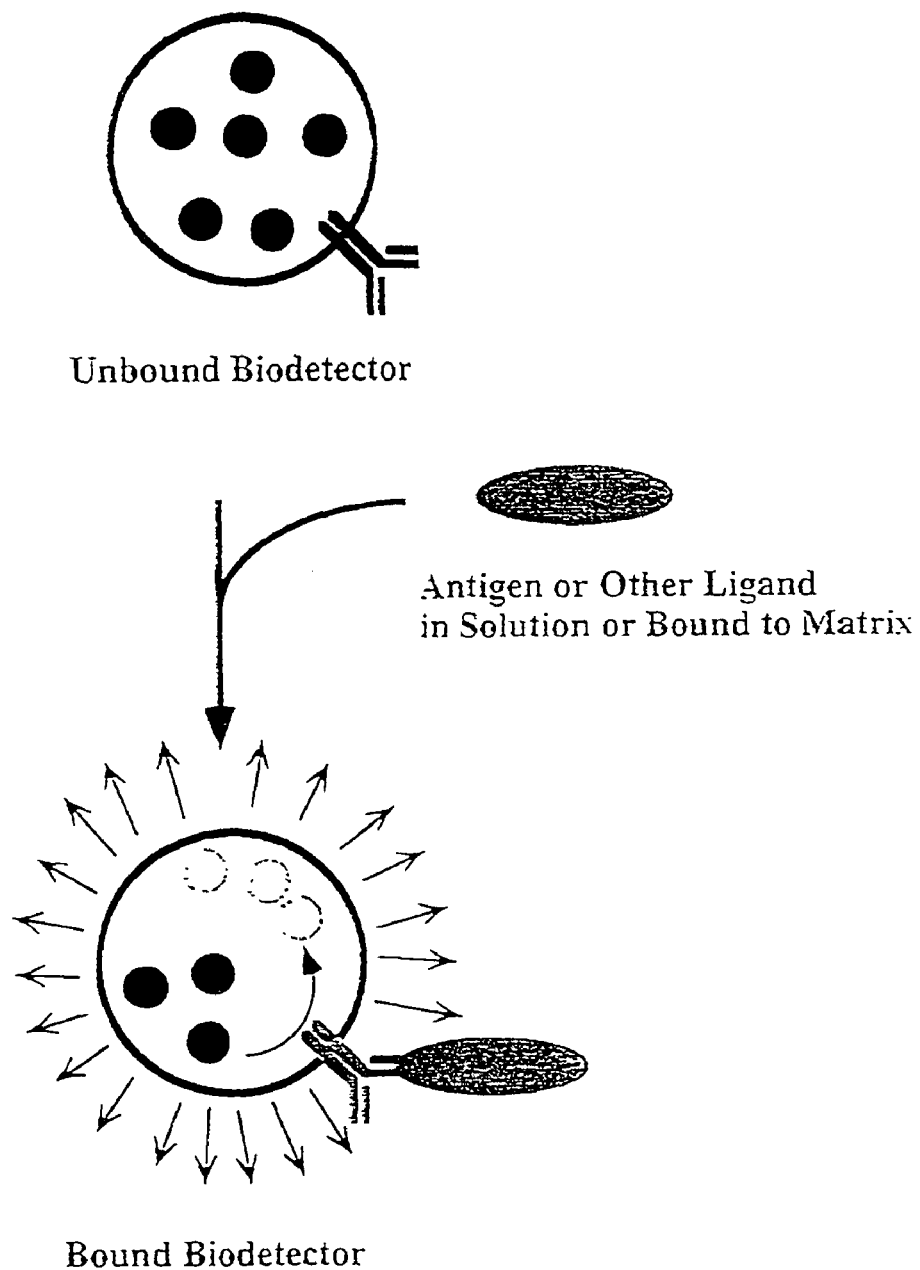
FIG. 1 depicts a generic model demonstrating the main components of a biodetector. A biodetector consisting of an entity possessing sensing ("Y-shaped structure on surface"), transducing components (part of "Y-shaped" structure inside of biodetector) and light-emitting components (small circles).

The generic mechanism of a ligand-specific biodetector is shown in FIG. 1.

Figure 2:
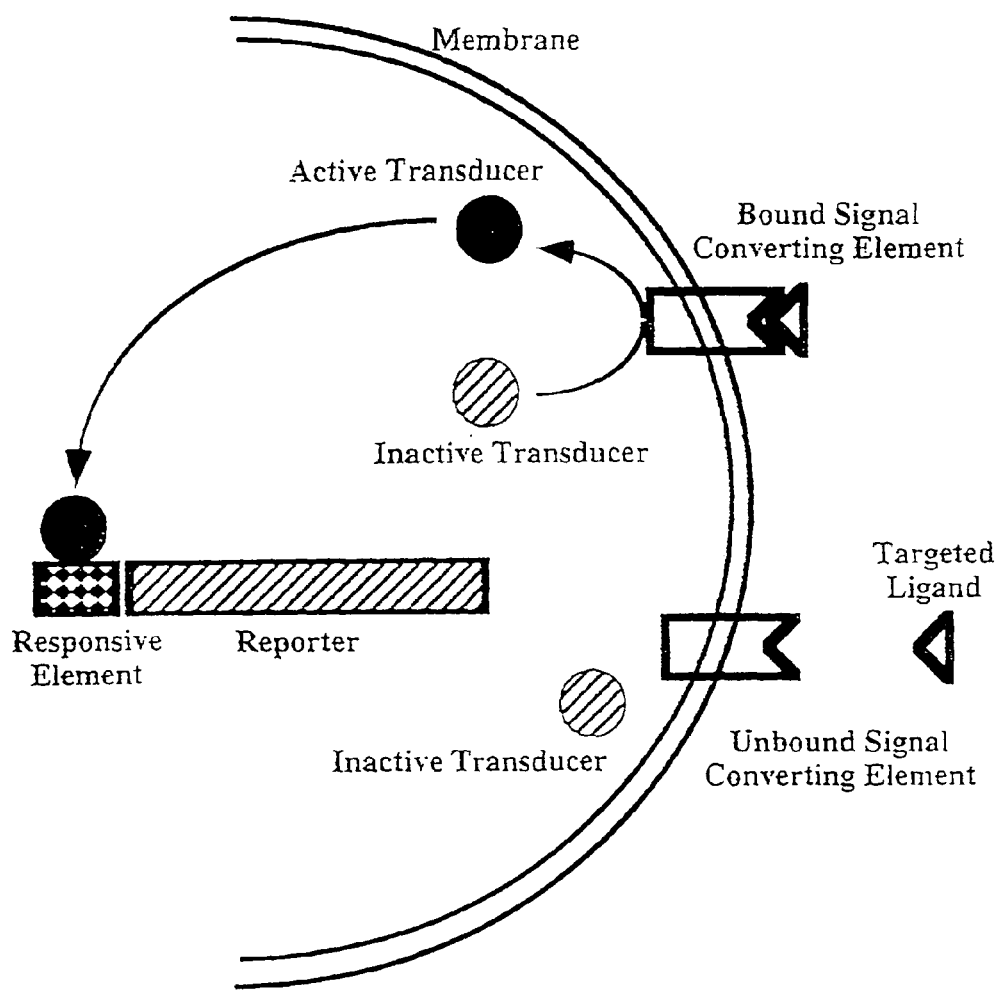
FIG. 2 depicts a more specific scheme of a biodetector on the molecular level.

FIG. 2 shows the molecular mechanism of a preferred biodetector more specifically. In the depicted example, the biodetector is a bacterial cell expressing a transmembrane target specific signal converting element, comprising an extracellular ligand-specific binding moiety, e.g., an antibody, which is coupled to an intracellular signal transforming domain. The target specific signal converting element is integrated in a membrane, e.g., a bacterial membrane, which separates an "extracellular" compartment from an "intracellular" compartment. The ligand-specific moiety is capable of binding to a selected substance, which triggers the activation of the intracellular signal transforming domain. The activated intracellular signal transforming domain in turn converts an inactive transducer into an active transducer. The transducer is characterized by its capability to bind, when converted to its active form, to a promoter element, which is operatively linked to a reporter gene. Transcription and translation of the reporter gene or operon results in a gene product which produces a detectable signal, such as light. In preferred embodiments of the invention, the reporter is a luciferase operon, which produces visible light and can easily be monitored, measured and quantified with high sensitivity.

Alternatively, the signal transforming domain could act directly on a modified reporter molecule. The reporter molecule would be modified to be expressed in an inactive state which can then be activated through its interaction with the signal transforming domain directly.

The biodetectors, providing a "light switch" that responds to a predetermined selected substance presents a number of advantages over current methodologies. First, the switch allows for detection of antigens, present in complex mixtures and eliminates the need to wash off unbound antibodies, thus simplifying the detection. Since ligand bound to antibody turns on light and since there is no background light in the sample, no washing is necessary to reduce signal to noise ratio, reduced noise increases sensitivity, and only specific interaction turns on the light.

Once bound to a ligand, an enzymatic cascade is activated that serves to transmit the signal.

Moreover, if the targeted ligand is abundantly expressed on the surface of, for example, pathogenic microbes, many biodetecting bacteria will bind to a single target, thus serving to amplify the signal and result in extremely sensitive detection systems.

Furthermore, as the ligand-specific domain of the signal converting element of the biodetector system may be exchanged like a cassette, an unlimited number of biodetectors can be generated to recognize any desired or selected substance. Thus, the biodetectors of the present invention provide a flexible, generic system that be can adapted to recognize any selected substance, out of a wide variety of choices. Biodetectors targeting a substance of interest can rapidly be developed.

Figure 3:
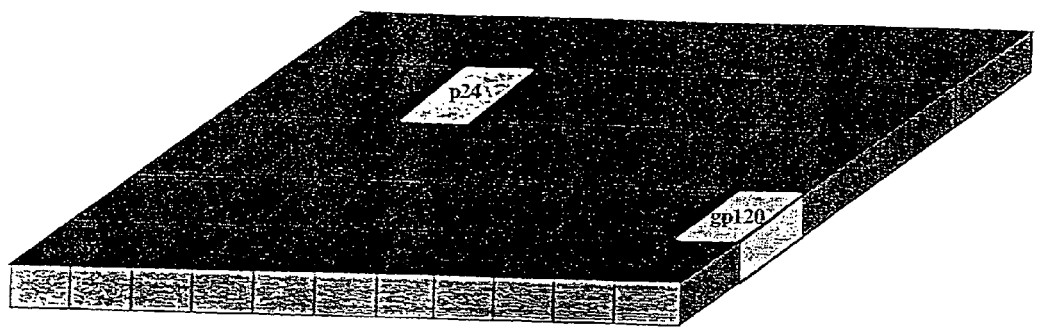
FIG. 3 depicts an ordered array of biodetectors on a solid support such that a variety of substances in a sample can be detected simultaneously.

The biodetectors of the invention are versatile as they are effective in vivo, in solution, or on fixed sensor plates. Furthermore, arrays of these biodetectors may be constructed, operating at different wavelengths or on different positions of a "biosensor chip", allowing for simultaneous monitoring and screening of multiple agents, genes, gene products, or other targets. See, FIG. 3. For example, the biodetectors may be assembled in a unique multi-detector array configuration for the purpose of constructing a system capable of a broad ranging, powerful analysis in a single step. For example, the biodetector may be placed on a gel that lies on top of a normal signal detecting instrument, which, in the case the generated signal is light, may be, e.g., a charge coupled device (CCD) chip. Due to the spatial recognition of signals by the CCD array, the biodetector array may provide for a light-based analysis using multiple different sensors placed in an array on one sensor chip. Thus, an analysis may be simultaneously performed for, e.g., blood type, HIV exposure, Hepatitis status, Lymphokine profiles and CMV positively. Multiple types of infection to be rapidly and simultaneously screened.

If light is the signal produced by the reporter, the signal may be detected non-invasively, as light can be detected through, for example, tissue. See, co-pending U.S. patent application Ser. No. 08/270,631, hereby incorporated by reference in its entirety.

Furthermore, as the biodetectors of the invention are biocompatible, and as such environmentally friendly, they have comparatively low developmental costs and a lower burden to the user, especially when compared with methods that may involve toxic waste, such as radioactivity-based assays.

A further significant advantage of the biodetectors of the invention is the reduction in time and labor needed to perform many diagnostics tests. A common, rate-limiting step in many testing and diagnostic fields is the need for an accurate sensing and detection system suitable for providing immediate information. Examples include screening of the blood supply for the MDS virus and other blood borne pathogens, the study and evaluation of novel drugs in tissue culture or animal models, and the monitoring of therapeutic protein output after genetic therapy. For example, the mandatory screening of the blood supply for HIV and other agents currently requires numerous tests. An inexpensive, rapid, and specific sensor detecting numerous blood borne pathogens with built-in confirmatory tests could significantly streamline the process, thus reducing net cost to the user. Similarly, the evaluation of potential new drugs, known as lead compounds, by pharmaceutical companies now requires elaborate, expensive tissue culture and animal trials. An inexpensive sensor and related hardware to allow in vitro and in vivo monitoring of drug kinetics and effectiveness will have great value to drug companies searching for ways to streamline such lead compound development.

In sum, the biodetectors of the invention provide numerous advantages over currently available diagnostic detection systems.

1. Entities Sheltering Biodetectors

The biological components of the biodetector may be contained in or otherwise may be attached to living or nonliving entities that stabilize the essential interactions. Configuration of these components as such results in a micro sensing system capable of detecting small numbers of ligands with great specificity and sensitivity.

Living Entities

Most typically, the biodetector entity is a living cell which is genetically engineered to comprise all required components. Living entities include, but are not limited to, prokaryotes, eukaryotes, viruses, retroviruses, vectors, plasmids, phage, transformed eukaryotic cells, such as lymphocytes, macrophages, established cell lines. Most typically, the entity sheltering a genetically engineered bacterial cell, as *E. coli*. Genetically-modified bacteria can be grown rapidly at low cost, thus the advantage of the use of living cells as biodetector entity is that pools of these biodetectors can be replicated and grown once the original biodetector is constructed.

The use of "living" biodetector entities has several advantages. First, it allows the growth of biodetectors at low cost, once the sensors are engineered. Second, it allows a system wherein a detector can grow and continue to develop within a tissue, rather than wearing out as would a conventional inorganic sensor. Third, a living biodetector can amplify the detected signal. For example, the binding of one antigen to the surface of the bacteria can trigger a series of light-generating substances to be made, each of which can produce light in a repetitive manner. Thus, the binding of one antigen that properly stimulates the system can result in the production of large amounts of photons from one living biosensor. Forth, as these biosensors may bind in large numbers to a target, the result is that many biodetectors, i.e., bacteria, with each amplifying the binding event, leading to a high degree of amplification. Thus, extremely high sensitivity can be achieved.

Non-Living Entities

However, abiotic biodetectors may be generated as well. The biodetector system may be placed in an inanimate gel, in abiotic capsules and liposomes and as such be injected into the body, or mounted on plates. Further, any other entity capable of preserving vectoral metabolism such as a lipid bilayer may be employed.

2. The Signal-Converting Element

The signal converting element is composed of an "extracellular" portion selectively binding a specific substance and an "intracellular" portion capable of activating the transducer. Typically, the signal converting element will be a transmembrane fusion protein composed of an extracellular ligand-binding portion, e.g. an antibody and an intracellular enzymatic portion, which is activated upon binding of the extracellular portion to a the selected target. Accordingly, the signal converting element is designed to convert the recognizing and binding of a specific substance, i.e., ligand and into a intracellular signal, resulting in the activation of the transducer component, which in turn, activates a promoter that drives the expression of the reporter protein.

The Ligand-Binding Domain

Substances which may be identified by the present invention include, but are not limited to, proteins, peptides, sugars, fatty acids, ions, microorganisms, including bacteria, viruses and retroviruses. Accordingly, the ligand-binding domain may be an antibody, an antibody fragment, cellular receptor or any other ligand binding protein, such as *Staphylococcus* Proteins A and G, a macrophage Fc receptor, a carbohydrate moiety, or an ion-binding moiety, such as domains from sodium or potassium channels.

In specific embodiments, the ligand-binding domain is an antibody or a derivative thereof, including but not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. In particular the monoclonal antibody technology and the more recent development of techniques for expressing functional antibodies in bacterial cells have increased the versatility and ease of identifying suitable ligand-binding domains for any desired target. For details about the expression of antibodies in bacterial cells, see, among other places, Collet et al., 1992, *Proc. Natl. Acad. Sci. U.S.A.* 89:10026-10030, and Huse et al., 1989, *Science* 246:1275-1281.

Moreover, the source of the antibody coding regions is not limited to those cloned from hybridoma cell lines where the specificity of the antibody is known and is monoclonal in nature. Rather, large antibody libraries may be employed to generate the fusion proteins such that a large number of biodetectors for the detection of an indefinite range of antigens can be generated.

The Signal Transforming Domain

The signal transforming domain may consist of an enzyme or active domain of an enzyme that has any number of protein modifying functions which may include phosphorylation, dephosphorylation, methylation, acetylation and protease activity. Such enzymes include protein kinases, phosphorylases, protein methylases, acetylases, proteases, proteinase K, serine proteases among others. In a specific embodiment of this patent the active domain of the bacterial phosphorylase, PhoQ, will be fused in a gene fusion to a region of a heavy chain antibody cDNA. As such, interaction of the expressed fusion protein with the targeted antigen (ligand) will result in a conformational change in the antibody-phosphorylase fusion that will activate the specific phosphorylase activity which activates PhoP, a transducer protein, through a phosphorylation/dephosphorylation event. Active PhoP activates the Pho promoter which is used to drive expression of the reporter operon lux. The transducer activating domain of the signal converting element is characterized in that it changes conformation or electronic charge upon binding a specific molecule, which results in activation of the transducer. The transducer may be activated by phosphorylation, glycosylation, methylation electron transport, hydrogen transport, carboxylation, dehydrogenation, oxidation/reduction or any other chemical modification.

3. Transducers

The transducer is activated by the signal converting element upon ligand binding. The transducer may be any molecule that can recognize and respond to a change in conformation, electrical charge, addition or subtraction of any chemical subgroup, such as phosphorylation, glycosylation, and in turn is capable of triggering a detectable response.

In specific embodiments of the invention, activation of the transducer triggers, directly or indirectly, the activation of a transcription activating element, e.g., a promoter, to effect the activation of a reporter gene or reporter operon. Transcription and translation of the reporter gene or operon in turn results in a gene product or gene products which produces a detectable signal, such as light. However, in alternative embodiments, activation of the transducer may directly result in a visible and measurable signal.

4. Reporter Genes and Operons

A wide range of reporter genes or reporter operons may be employed, including such which result in bioluminescence, colorimetric reactions or fluorescence. For example, reporter genes may encode for pigments (Bonhoeffer, 1995, *Arzneimittelforschung* 45:351-356) such as bacterial rhodopsin (Ng et al., 1995, *Biochemistry* 34:879-890), melanin (Viticin et al., 1994, *Photochemistry and Photobiology* 59:455-462), aquorins (Molecular Probes, Seattle), green fluorescent protein (GFP, Clonetech, Palo Alto; Chalfie et al., 1994, *Science* 263:802-805; Cubitt et al., 1995, *TIBS* 20:448-455), yellow fluorescent protein (Daubner et al., 1987, *Proc. Natl. Acad. Sci. U.S.A.* 84:8912-8916), flavins, bioflavinoids, hemoglobin (Chance et al., 1995, *Analytical Biochemistry* 227:351-362; Shen et al., 1993, *Proc. Natl. Acad. Sci. U.S.A.* 90:8108-8112), heme (Pieulle et al., 1996, *Biochem. Biophys. Acta* 1273: 51-61), indigo dye (Murdock et al., 1993, *Biotechnology* 11:381-386), peridinin-chlorophyll-a protein (PCP) (Ogata et al., 1994, *FEBS Letters*, 356:367-371), or pyocyanine (al-Shibib and Kandela, 1993, *Acta Microbiologica Polonica* 42:275-280). Alternatively, reporter genes may encode for enzymes that can cleave a color absorbing substrate such as β-lactamase, luminescent and fluorescent proteins, enzymes with fluorescent substrates, or any other gene that encodes an optically active chemical or that can convert a substrate to an optically active compound. In a further alternative, reporter genes may encode photoproteins. In each case, the reporter is operatively linked to an inducible promoter which is activated by the active form of the transducer component.

In a specific embodiment of the invention, bioluminescent reporters are employed.

Bioluminescence-Based Reporter Genes and Operons

Several types of bioluminescent reporter genes are known, including the luciferase family (e.g., Wood et al., 1989, *Science* 244:700-702). Members of the luciferase family have been identified in a variety of prokaryotic and eukaryotic organisms. Luciferase and other enzymes involved in the prokaryotic luminescent (lux) systems, as well as the corresponding lux genes, have been isolated from marine bacteria in the *Vibrio* and *Photobacterium* genera and from terrestrial bacteria in the *Xenorhabdus* genus, also called photorhaldus.

An exemplary eukaryotic organism containing a luciferase system (luc) is the North American firefly *Photinus pyralis*. Firefly luciferase has been extensively studied, and is widely used in ATP assays. cDNAs encoding luciferases from *Pyrophorus plagiophthalamus*, another species, click beetle, have been cloned and expressed (Wood et al., 1989, *Science* 244: 700-702). This beetle is unusual in that different members of the species emit bioluminescence of different colors. Four classes of clones, having 95-99% homology with each other, were isolated. They emit light at 546 nm (green), 560 nm (yellow-green), 578 nm (yellow) and 593 nm (orange).

Luciferases requires a source of energy, such as ATP, NAD (P)H, and the like, and a substrate, such as luciferin, decanal (bacterial enzymes) or coelentrizine and oxygen.

The substrate luciferin must be supplied to the luciferase enzyme in order for it to luminesce. Thus, a convenient method for providing luciferin is to express not only the luciferase but also the biosynthetic enzymes for the synthesis of the substrate decanal. Oxygen is then the only extrinsic requirement for bioluminescence, in bacteria expressing these proteins from the Lux operon.

For example, the lux operon obtained from the soil bacterium *Xenorhabdus* luminescence (Frackman et al., 1990, *J. Bact.* 172:5767-5773) may be used as reporter operon, as it confers on transformed *E. coli* the ability to emit photons through the expression of the two subunits of the heterodimeric luciferase and three accessory proteins (Frackman et al., supra).

Optimal bioluminescence for *E. coli* expressing the lux genes of X. luminescence is observed at 37° C. (Szittner and Meighen 1990, *J. Biol. Chem.* 265:16581-16587; Xi et al., 1991, *J. Bact.* 173:1399-1405), which contrasts the low temperature optima of luciferases from eukaryotic and other prokaryotic luminescent organisms (Campbell, 1988, *Chemiluminescence. Principles and Applications in Biology and Medicine* (Chichester, England: Ellis Horwood Ltd. and VCH Verlagsgesellschaft mbH)). Thus, the reporter operon may be chosen according to the nature and the requirements of a specific application. For example, the luciferase from X. luminescence, therefore, is well-suited for use as a marker for studies in animals.

Luciferase vector constructs can be adapted for use in transforming a variety of host cells, including most bacteria, and many eukaryotic cells. In addition, certain viruses, such as herpes virus and vaccinia virus, can be genetically-engineered to express luciferase. For example, Kovacs and Mettenleiter, 1991, *J. Gen. Virol.* 72:2999-3008, teach the stable expression of the gene encoding firefly luciferase in a herpes virus. Brasier and Ron, 1992, *Meth. in Enzymol.* 216: 386-396, teach the use of luciferase gene constructs in mammalian cells. Luciferase expression from mammalian cells in culture has been studied using CCD imaging both macroscopically (Israel and Honigman, 1991, *Gene* 104:139-145) and microscopically (Hooper et al., 1990, *J. Biolum. and Chemilum.* 5:123-130).

C. Imaging of Light-Emitting Biodetectors

Light emitting biodetectors may be imaged in a number of ways. Guidelines for such imaging, as well as specific examples, are described below.

1. Photodetector Devices

In one embodiment of the present invention where the signal generated by the biodetector is light, an important aspect will be the selection of a photodetector device with a high enough sensitivity to enable the imaging of faint light. Furthermore, in cases where the biodetector is used in a living subject, the imaging has to be in a reasonable amount of time, preferably less than about thirty (30) minutes, and to use the signal from such a device to construct an image.

In cases where it is possible to use light-generating moieties which are extremely bright, and/or to detect light-emitting conjugates localized near the surface of the subject or animal being imaged, a pair of "night-vision" goggles or a standard high-sensitivity video camera, such as a Silicon Intensified Tube (SIT) camera (e.g., Hamamatsu Photonic Systems, Bridgewater, N.J.), may be used. More typically, however, a more sensitive method of light detection is required.

At extremely low light levels, such as those encountered in the practice of the present invention, the photon flux per unit area becomes so low that the scene being imaged no longer appears continuous. Instead, it is represented by individual photons which are both temporally and spatially distinct form one another. Viewed on a monitor, such an image appears as scintillating points of light, each representing a single detected photon.

By accumulating these detected photons in a digital image processor over time, an image can be acquired and constructed. Alternatively, the scintillating points can be enumerated and reported numerically obviating the image reconstruction step thus expediting the analysis. In contrast to conventional cameras where the signal at each image point is assigned an intensity value, in photon counting imaging the amplitude of the signal carries no significance. The objective is to simply detect the presence of a signal (photon) and to count the occurrence of the signal with respect to its position over time.

At least two types of photodetector devices, described below, can detect individual photons and generate a signal which can be analyzed by an image processor.

Reduced-Noise Photodetection Devices

The first class constitutes devices which achieve sensitivity by reducing the background noise in the photon detector, as opposed to amplifying the photon signal. Noise is reduced primarily by cooling the detector array. The devices include charge coupled device (CCD) cameras referred to as "back-thinned", cooled CCD cameras. In the more sensitive instruments, the cooling is achieved using, for example, liquid nitrogen, which brings the temperature of the CCD array to approximately –120° C. The "backthinned" refers to an ultra-thin backplate that reduces the path length that a photon follows to be detected, thereby increasing the quantum efficiency. A particularly sensitive backthinned cryogenic CCD camera is the "TECH 512", a series 200 camera available from Photometrics, Ltd. (Tucson, Ariz.).

Photon Amplification Devices

A second class of sensitive photodetectors includes devices which amplify photons before they hit the detection screen. This class includes CCD cameras with intensifiers, such as microchannel intensifiers. A microchannel intensifier typically contains a metal array of channels perpendicular to and co-extensive with the detection screen of the camera. The microchannel array is placed between the sample, subject, or animal to be imaged, and the camera. Most of the photons entering the channels of the array contact a side of a channel before exiting. A voltage applied across the array results in the release of many electrons from each photon collision. The electrons from such a collision exit their channel of origin in a "shotgun" pattern, and are detected by the camera.

Even greater sensitivity can be achieved by placing intensifying microchannel arrays in series, so that electrons generated in the first stage in turn result in an amplified signal of electrons at the second stage. Increases in sensitivity, however, are achieved at the expense of spatial resolution, which decreases with each additional stage of amplification.

An exemplary microchannel intensifier-based single-photon detection device suitable for the practice of the invention is the C2400 series, available from Hamamatsu.

Image Processors

Signals generated by photodetector devices which count photons need to be processed by an image processor in order to construct an image which can be, for example, displayed on a monitor or printed on a video printer. Such image processors are typically sold as part of systems which include the sensitive photon-counting cameras described above, and accordingly, are available from the same sources (e.g., Photometrics, Ltd., and Hamamatsu). Image processors from other vendors can also be used, but more effort is generally required to achieve a functional system.

The image processors are usually connected to a personal computer, such as an IBM-compatible PC or an Apple Macintosh (Apple Computer, Cupertino, Calif.), which may or may not be included as part of a purchased imaging system. Once the images are in the form of digital files, they can be manipulated by a variety of image processing programs (such as "ADOBE PHOTOSHOP", Adobe Systems, Adobe Systems, Mountain View, Calif.) and printed.

2. Constructing an Image of Photon Emission

In cases where, due to an exceptionally bright light-generating moiety and/or localization of light-emitting conjugates near the surface of the subject, a pair of "night-vision" goggles or a high sensitivity video camera was used to obtain an image, the image is simply viewed or displayed on a video monitor. If desired, the signal from a video camera can be diverted through an image processor, which can store individual video frames in memory for analysis or printing, and/or can digitize the images for analysis and printing on a computer.

Alternatively, if a photon counting approach is used, the measurement of photon emission generates an array of numbers, representing the number of photons detected at each pixel location, in the image processor. These numbers are used to generate an image, typically by normalizing the photon counts (either to a fixed, pre-selected value, or to the maximum number detected in any pixel) and converting the normalized number to a brightness (grayscale) or to a color (pseudocolor) that is displayed on a monitor. In a pseudocolor representation, typical color assignments are as follows. Pixels with zero photon counts are assigned black, low counts blue, and increasing counts colors of increasing wavelength, on up to red for the highest photon count values. The location of colors on the monitor represents the distribution of photon emission, and, accordingly, the location of light-emitting conjugates.

In order to provide a frame of reference for the conjugates, a grayscale image of the (still immobilized) subject from which photon emission was measured is typically constructed. Such an image may be constructed, for example, by opening a door to the imaging chamber, or box, in dim room light, and measuring reflected photons (typically for a fraction of the time it takes to measure photon emission). The grayscale image may be constructed either before measuring photon emission, or after.

The image of photon emission is typically superimposed on the grayscale image to produce a composite image of photon emission in relation to the subject.

If it desired to follow the localization and/or the signal from a light-emitting conjugate over time, for example, to record the effects of a treatment on the distribution and/or localization of a selected biocompatible moiety, the measurement of photon emission, or imaging can be repeated at selected time intervals to construct a series of images. The intervals can be as short as picoseconds (in fast gated cameras) or seconds, to days or weeks with integrating cameras.

D. Applications

Specific applications of the biodetectors include the diagnosis of diseases, detection of clinically relevant substances, detection of environmental contaminants, detection of food contaminants. Further, the biodetectors of the invention will find numerous applications in basic research and development.

Diagnosis of Infectious Disease

The biodetectors may be used for the detection of antigens in body fluids, including blood or urine, or tissues and other fluids. Suitable target antigens include, but not limited to, bacterial pathogens, viral pathogens, fungal pathogens, serum proteins, lymphokines, cytokines, cytotoxins, interferons, $\beta$-2 microglobulin, immunoglobulins, peptides, and polypeptides.

Specific diagnostic tests targeting bacterial pathogens may include, but are not limited to, diagnosis of lyme disease, *Streptococcus, Salmonella, Tuberculosis, Staphylococcus,*

*Pseudomonas, Helicobactor, Listeria, Shigella, Proteus, Enterococci, Clostridium, Bordatella, Bartonella, Rickettsia, Chlamydia, Spirochetes.* Diagnostic tests targeting viral pathogens may include, but are not limited to, the detection of retroviruses, such as HIV-1, HTLV-1, hepatitis viruses (HBV, HCV, HAV), herpes viruses, including to EBV, CMV, herpes simplex I, herpes simplex II, and HHV-6, encephalitis, including Japanese encephalitis virus, Eastern and Western Encephalitis Virus, rotavirus, all known and yet to be identified human and animal viral pathogens and unconventional agents such as those associated with Alzheimer's and Crutzfeld-Jacob disease (prions). Targeting fungal pathogens may include, but are not limited to, *cryptococcus, histoplasmosis, coccidiodes, candida, giardia.*

Detection of Other Clinically Relevant Substances

Applications of the biodetectors may include the detection of clinically relevant substances, such as sugar molecules, fatty acids, proteins or microorganisms, in body fluids, e.g., blood or urine, or tissue. Targeted antigens may include enzymes indicating the proper function of organs, including lactate dehydrogenase, urea, glucose, and other small molecules, and cytokines. Alpha fetal protein may be targeted for the diagnosis of spinobifida. Certain bacterial species or other microorganisms may be targeted to measure their representation in mixed populations such as gut and vaginal flora. An important diagnostic target will be lymphokines for the diagnosis and prognosis of a range of diseases. With current methods, the profile of lymphokines cannot easily be determined, however, it can be expected that its determination will elucidate a wide array of unknown aspects about the relationship of diseases and disease states. Further, an important medical application will be the early, perinatal diagnosis of genetic diseases, including cystic fibrosis, sickle cell anemia, Down syndrome, phenylketonuria, ADA deficiency, thallassemias, growth hormone deficiency, predisposition of cancer. Finally, the biodetectors may find application in the real time monitoring of, e.g., glucose levels and drug levels.

Agricultural and Veterinary Applications

All above described medical applications may be applied to veterinary medicine.

Detection of Environmental Contaminants

For example, the biodetectors may be used for detection of contaminants in water supply. Selected targets may include, but are not limited to *Giardia, Cryptococcus, Legionella, Clostridia* toxins, *Enterobacter, E. coli*, protozoans, heavy metals. Further, representation of certain bacteria in soil populations may be measured by the means of the biodetectors; soil may be screened to track genetically engineered organisms that might have been released into the environment.

Detection of Food Contaminants

The biodetectors may be employed to identify contaminants in food, including, but not limited to bacteria, such as *salmonella, coliforms, staphylococcus, clostridium*, and fungi.

Basic Research and Development

The biodetectors will find numerous applications in basic research and development. Examples include detection system in standard immunoassay, such as Western Blots, ELISA, the determination of lymphokine profiles, the detection of cell culture contamination, including *Mycoplasma*. Further, the biodetectors will be useful as detection system in expression assays, for the detection of cell surface markers, such as CD4, CD8, adhereins.

Abiotic Biodetectors

For certain applications, when antigenicity is an issue (i.e., in vivo) abiotic biodetectors may be desirable. Examples include the in vivo detection and localization of infection, tissue damage and other pathologies. Encapsulation of the biodetector mechanism in generally inert vesicles bilayer or membranes or any other entity that is non-living and will preserve vectoral metabolism (such as liposomes) in such way that contact with ligands results in light will permit the use of this system in vivo.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VII. EXAMPLES

The first three examples are three approaches which may be employed to link the signal transduction to the expression of a specific gene.

A. Example 1

Linking Signal Transduction to the Regulation of a Specific Genes (Approach 1)

The following example illustrates an approach which can be used to link the signal transduction to regulation of a specific gene.

A transposon is constructed to identify promoters that are activated by ligand binding to surface expressed ligand-binding molecules, e.g., antibodies. Promoterless reporter systems have been employed for identifying a variety of regulatory sequences in bacteria. Ronald et al., 1990, *Gene* 90:145-148. The transposon consists of (i) (1) a promoterless operon containing the genes for bioluminescence, (2) a selectable marker (kanamycin resistance gene; Kan), and (3) a negative regulator (the lambda repressor); (ii) an additional selectable marker (chloramphenicol resistance gene; Ch1) expressed by the lambda operator; and (iii) a third selectable marker that is constitutively expressed (ampicillin resistance gene; Amp). Bacterial cells expressing the antibody of interest are transformed with the transposon. The conformational change in the transmembrane antibody-fusion protein signals the activation or chemical modification of the transducer which is designed to relay that message to the promoter region of the lux construct. Positive transformants are selected by determination of the acquired Amp resistance. Cells containing the transposon behind promoters that are active in the presence of antigen (including constitutive expression) will be Kan resistant in the presence of antigen, and cells containing a transposon behind promoters that are off in the absence of antigen will be Ch1 resistant in the absence of antigen. Therefore by passage through a series of growth conditions the desired transformants that appropriately express luciferase in response to antigens will be identified. The promoters can then be characterized and used to construct additional biodetectors.

FIG. 4 depicts a biodetector generated as described in EXAMPLE 1. As shown in FIG. 4A, in the absence of antigen, the fusion protein does not transduce a signal to the promoter which drives expression of the cloned genes encoded by the integrated transposon. Therefore, the phenotype of the proposed *E. coli*, in the absence of antigen, is ampicillin resistant, chloramphenicol resistant, kanamycin sensitive, and not bioluminescent. Ampicillin resistance is constitutively expressed to maintain selection of the integrated transposon.

When, however, the promoter is turned on by binding of the activated transducer, which is activated by ligand binding to the fusion protein, the luciferase operon, the kanamycin resistance gene, and the lambda repressor are expressed. The lambda repressor acts on the lambda operator, thereby shutting down the expression of the chloramphenicol resistance gene. In the presence of antigen the phenotype of the cells is therefore characterized by ampicillin resistance, kanamycin resistance, chloramphenicol sensitivity, and bioluminescence.

Thus, induction and activation of genes as described above permits positive selection for the desired response to antigen. More specifically, only those bacterial cells which integrate the described transposon at a suitable site in the genome survive the selection procedures while nonresponsive bacteria die.

B. Example 2

Linking Signal Transduction to the Regulation of a Specific Genes (Approach 2)

The following example illustrates an second approach which can be used to link the signal transduction to regulation of a specific gene.

The fusion protein composed of an antibody heavy chain and a surface protein known to transduce signals for gene regulation, and a promoter that is affected by this signal is placed in front of the marker gene. Antibody light chains are coexpressed in the biodetector to provide additional ligand specificity (Borrebaeck et al., 1992, *Biotechnology* 10:697-698). Bacterial phosphatase has been selected as the initial transmembrane and signal-transducing component of the gene fusion because of its current use in identifying surface expressed fusion proteins in bacteria (Kohl et al., 1990, *Nucleic Acids Res.* 18:1069; Weiss and Orfanoudakis, 1994; *J. Biotechnol.* 33:43-53) and a colorimetric substrate is available for measuring phosphatase activity. Antibody fragment-phosphatase fusions have been generated with retention of both ligand binding specificity and phosphatase activity (Kohl et al., 1991, *Acad. Sci.* 646:106-114; Wels et al., 1992, *Biotechnology* 10:1128-1132). Phosphatase-antibody fusions have been used to generate labeled antibodies for immunoassay (Carrier et al., 1995, *J. Immunol. Methods* 181: 177-186; Ducancel et al., 1993, *Biotechnology* 11:601-605; Weiss et al., 1994, *J. Biotechnol.* 33:43-53; Weiss and Orfanoudakis, 1994, *J. Biotechnol.* 33:43-53; Wels et al., 1992, *Biotechnology* 10:1128-1132). In addition, antibodies to modified bacterial phosphatase have been shown to alter phosphatase function (Brennan et al., 1995, *Proc. Natl. Acad. Sci. U.S.A.* 92:5783-5787), indicating that protein-protein interactions can modulate phosphatase activity most likely through conformational changes in the phosphatase molecule. Expression of phosphatase fusion proteins on bacterial cell surfaces transduces a signal, phosphorylation into the cell which induces expression of specific genes. This system may be modified to tightly link the expression of the marker proteins, luciferase and its accessory proteins, to binding of the ligand to the antibody-phosphatase fusion protein, i.e., a ligand-dependent molecular switch.

C. Example 3

Linking Signal Transduction to the Regulation of a Specific Genes (Approach 3)

The following example illustrates an third approach which can be used to link the signal transduction to regulation of a specific gene.

The approaches described in EXAMPLE 1 and 2 may be combined using the transposon described above in cells expressing the phosphatase-antibody fusions.

A bacterial strain is established that has a reporter gene linked to an inducible promoter that responds specifically to the activation of a transducer molecule for example, those of the pho operon. An antibody repertoire library cloned into an vector that will fuse the antibody to a pho membrane protein can then be put into the above bacterial strain. This library of biodetectors can then be tested against specific molecules that are of interest to detect and selection of the appropriate biodetector can be made. This resulting biodetector can then be propagated in large amounts.

D. Example 4

Detection of Substances in Solution

The following is an illustrative assay to detect ligands including viral and bacterial antigens in solutions such as whole blood and plasma.

Samples containing the ligand to be detected and quantified are diluted (2 fold serial dilutions) in 96 well plates along with reference standards. The specific biodetector is added to each of the wells as a viable active cell, and analyzed immediately. Bioluminescent signals from the plate are detected using a charge coupled device (CCD camera) or a luminometer in a 96 well format. Relative bioluminescence from the unknown samples are plotted on a standard curve for quantitation.

E. Example 5

Detection of Substances on Solid Support

The following is an illustrative assay to detect substances on solid supports such as nitrocellulose or nylon membranes, e.g., in Western blot analyses using specific biodetectors.

Following transfer of the proteins to a solid support (PVDF Immobilon membrane, Millipore) using standardized procedures, the membrane is dried and transferred to a dish containing the specific biodetector, as a biological active cell, in minimal medium or other clear buffer containing nutrients for bacterial metabolism. After 30 minutes incubation at room temperature, the membrane is removed sealed, while still wet, in a zip lock or heat sealable plastic bag. Bioluminescent signal from the biodetectors bound to the membrane is detecting using an X-ray film, a CCD detector, or other light sensitive detection methods. Signals can be quantified using standard image analysis software.

F. Example 6

Effect of Human Blood on the Light Emission from Bioluminescent *Salmonella*

As demonstrated in the following example, fewer than ten (10) bacterial cells can be detected with an intensified CCD detector.

Two fold serial dilutions of *Salmonella*, strain LB5000, that had been transformed with a plasmid that conferred constitutive expression of the luciferase operon were plated in duplicate into 96 well plates. Dilutions were made in 30 µl of growth medium alone (indicated as LB5000) and with 30 µl of blood to determine the effects of blood as a scattering and absorbing medium on the limits of detection. Each dilution and the numbers of colony forming units (CFU) implied from plating samples from concentrated wells are indicated in FIG. 5. The relative bioluminescence for each well as determined by analysis of the image generated by the CCD detector is shown (FIG. 5). The signal in the more concentrated wells was off scale and the numbers are therefore not linear at higher concentrations.

All references are incorporated in their entirety.

The invention claimed is:

1. A biodetector for the detection of a selected substance comprising:
   (a) a transmembrane fusion protein comprising an extracellular ligand-specific moiety and a protein-modifying membrane intracellular enzymatic signal transforming domain, wherein said extracellular ligand-specific moiety comprises an antibody and wherein said antibody binds said selected substance, which binding activates said intracellular enzymatic signal transforming domain, wherein the membrane intracellular enzymatic signal transforming domain is a kinase;
   (b) a transducer protein, wherein said transducer has an inactive form and an active form which are distinct from each other, and said activated intracellular enzymatic signal transforming domain converts said inactive form of said transducer into said active form of said transducer protein, wherein said transducer and said intracellular enzymatic signal transforming domain are separate proteins;
   (c) a responsive element comprising a nucleic acid encoding a light-generating protein operably linked to a transcription activation element, wherein said responsive element is bound by and activated by said active form of said transducer, resulting in a detectable light signal.

2. The biodetector of claim 1, wherein said light-generating protein is a bioluminescent or fluorescent protein.

3. The biodetector of claim 2, wherein said light-generating protein is a bioluminescent protein.

4. The biodetector of claim 2, wherein said nucleic acid comprises a luciferase operon.

5. The biodetector of claim 4, wherein said selected substance is selected from the group consisting of microorganism, virus, retrovirus, protein, sugar and ion.

6. The biodetector of claim 1, wherein said intracellular enzymatic signal transforming domain is a PhoQ intracellular enzymatic domain.

7. A genetically engineered bacterial cell comprising a biodetector according to claim 1.

8. The biodetector of claim 1, wherein said intracellular enzymatic signal transforming domain comprises an active domain of PhoQ.

9. The biodetector of claim 1, wherein said transmembrane fusion protein is a fusion of an active domain of PhoQ, and a region of a heavy chain antibody.

* * * * *